(12) United States Patent
Kao et al.

(10) Patent No.: US 6,906,797 B1
(45) Date of Patent: Jun. 14, 2005

(54) SIDE LIGHT ACTIVATED MICROFLUID CHANNELS

(75) Inventors: Hung Pin Kao, San Ramon, CA (US); Xing Yang, Mountain View, CA (US)

(73) Assignee: Aclara Biosciences, Inc., Mountain View, CA (US)

(*) Notice: Subject to any disclaimer, the term of this patent is extended or adjusted under 35 U.S.C. 154(b) by 1003 days.

(21) Appl. No.: 09/660,992

(22) Filed: Sep. 13, 2000

Related U.S. Application Data

(60) Provisional application No. 60/153,644, filed on Sep. 13, 1999.

(51) Int. Cl.[7] .................................................. G01J 3/30
(52) U.S. Cl. ....................... 356/317; 204/451; 204/452; 356/436; 356/318
(58) Field of Search ................................. 356/436, 317, 356/318, 311, 246, 344; 204/451, 452, 453, 602, 603; 435/286.5; 250/458.1

(56) References Cited

U.S. PATENT DOCUMENTS

| | | | |
|---|---|---|---|
| 4,863,560 A | | 9/1989 | Hawkins |
| 5,006,202 A | | 4/1991 | Hawkins et al. |
| 5,637,458 A | * | 6/1997 | Frankel et al. .................. 435/6 |
| 5,738,757 A | | 4/1998 | Burns et al. |
| 5,741,411 A | * | 4/1998 | Yeung et al. ................ 204/452 |
| 5,846,708 A | * | 12/1998 | Hollis et al. .................... 435/6 |
| 5,858,187 A | * | 1/1999 | Ramsey et al. ............. 204/452 |
| 5,948,227 A | * | 9/1999 | Dubrow ........................ 204/455 |
| 5,948,684 A | * | 9/1999 | Weigl et al. .................. 436/52 |
| 6,156,273 A | * | 12/2000 | Regnier et al. ................ 422/70 |
| 6,558,945 B1 | * | 5/2003 | Kao .......................... 435/287.2 |
| 6,660,149 B1 | * | 12/2003 | Karger et al. ................ 204/601 |
| 6,676,819 B1 | * | 1/2004 | Liu et al. ...................... 204/451 |
| 6,759,662 B1 | * | 7/2004 | Li ............................. 250/458.1 |

OTHER PUBLICATIONS

Backlund et al., "New shapes in (100) Si using KOH and EDP etches", *J. Micromech. Microeng.* 2:75–79,1992.

Sekimura et al., "Fabrication of 45° Optical Mirrors on (100) Silicon Using Surfactant–Added TMAH Solution", *International Conference on Solid State Sensors and Actuators*, pp. 550–551, Jun. 7–10, 1999.

Chang et al., "Mesa Structure Formation Using Potassium Hydroxide and Ethylene Diamine Based Etchants", *IEEE Workshop on Solid State Sensors and Actuators*, pp. 102–103, Hilton Head, SC, Jun. 1988.

Strandman et al., "Fabrication of 45° optical mirrors on (100) Si using wet anisotropic etching", *Proceedings of the Workshop on Micro Electrical Mechanical Systems (MEMS)*, vol. Workshop 8, pp. 244–249, Jan. 29, 1995.

* cited by examiner

*Primary Examiner*—Layla Lauchman
(74) *Attorney, Agent, or Firm*—Stephen C. Macevicz

(57) ABSTRACT

Devices are provided comprising reflecting channels for directing horizontally a vertical light beam through a multiplicity of streams. The devices provide particular applications in microfluidics, where streams of narrow cross-sectional dimensions are involved. Desirably, channels having 45° walls are provided for directing the beams and where the streams are divided by walls, the walls are at substantially 90°. Methods of fabrication of the devices are provided.

17 Claims, 7 Drawing Sheets

SIDE LIGHT ACTIVATED MICROFLUID CHANNELS

CROSS-REFERENCE TO RELATED APPLICATIONS

This application claims the benefit of the filing date of U.S. provisional application 60/153,644 filed Sep. 13, 1999, which disclosure is hereby incorporated by reference.

TECHNICAL FIELD

The field of this invention is irradiation and detection of light emitting entities in microchannels and the fabrication of devices for this purpose.

BACKGROUND

Microfluidics employs small capillary channels or microchannels in a solid substrate to perform a wide variety of operations. By employing electrical fields with conductive fluids in the microchannels, very small volumes may be accurately moved, reagents mixed, and the presence of an entity of interest determined. In many applications, the determination is fluorescence. Fluorescence can provide for high sensitivity, allows for multiplexing, by detecting photons at different wavelengths; by appropriate use of combinations of fluorophores one can employ a single light source for excitation. In addition, there are a large number of different commercially available detection devices. In addition, many assays have been developed which depend upon the use of fluorescence, such as DNA sequencing, receptor assays dependent upon expression of green fluorescent protein, immunoassays employing a fluorescent label, etc.

In the case of microfluidics, the use of plastics as the substrate has found application. While plastics have the advantage of ease of fabrication, cost and ready availability, they tend to be fluorescent. In addition, when irradiating a sample with excitation light, light scatter results in a significant background signal, particularly when the excitation pathway and emission pathway are the same. While some systems provide for an obtuse angle between the excitation and emission optical pathways, in the case of microfluidics there are the problems of directing the excitation light to the center of the microchannel, the small amount of sample that will be exposed to the irradiation and the substantially diminished fluorescent signal that one observes at an angle from the microchannel. Also, since the excitation light will encounter the device substrate, there is the further fluorescence of the substrate added to the fluorescent signal.

There is, therefore, an interest in designing new approaches to excitation of fluorophores in microchannels and detecting the fluorescent emission efficiently.

BRIEF DESCRIPTION OF RELEVANT ART

U.S. Patents of interest include U.S. Pat. No. 4,863,560, "Fabrication of Silicon Structures by Single Side, Multiple Step Etching Process"; U.S. Pat. No. 5,006,202, "Fabrication Method for Silicon Devices Using a Two Step Silicon Etching Process"; and U.S. Pat. No. 5,738,757, "Planar Masking for Multi-Depth Silicon Etching." Publications of interest include Backlund and Rosengren, "New shapes in (100) Si using KOH and EDP etches," J. Micromach. Microeng. 1992, 2:75–79; Sekimura and Naruse, Fabrication of 45° optical mirrors on (100) silicon using surfactant-added TMAH solution," International Conference on Solid State Sensors and Actuators, pp. 550–551, Sendai, Japan, Jun. 7–10, 1999; Strandman, et al., "Fabrication of 45° Mirrors Together with Well-Defined V-grooves Using Wet Anisotropic Etching of Silicon, J. of Microelectromechanical Systems (MEMS) and Chang and Hicks, "Mesa structure formation using potassium hydroxide and ethylene diamine based etchants." IEEE Workshop on Solid State Sensors and Actuators, pp. 102–103, Hilton Head, S.C., June 1988.

SUMMARY OF THE INVENTION

Methods and devices are provided for an optical system for emission detection from microchannels in plastic substrates. A master is formed for plastic molding of a microfluidic device, where the device has parallel fluid streams, optionally separated with at least substantially perpendicular side walls, and on each side of said streams is a microfabricated optic, having reflecting walls for directing a light beam through the streams and then into a waste light dump. The master is formed by separately etching different microstructures, with appropriate masking and different protective coatings, which are individually removed prior to final etching to provide deep microstructures. Microfabrication techniques are provided for molding microfluidic devices employing the optical system for use in fluorescent based operations.

DESCRIPTION OF THE SPECIFIC EMBODIMENTS

Figure 1A:
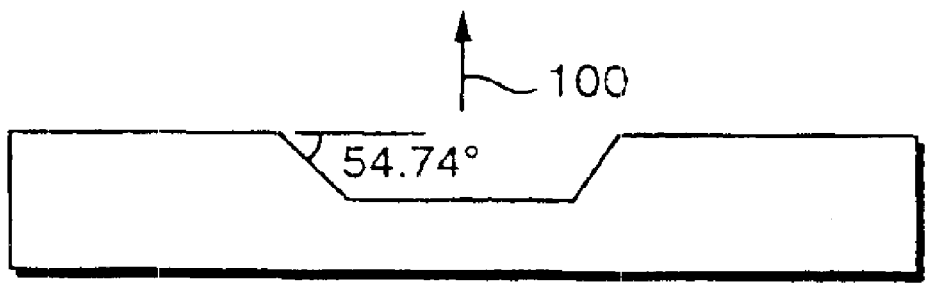
FIG. 1 is a diagrammatic side view of an etched silicon wafer.

The subject invention provides microfluidic devices comprising optical systems, methods of making the microfluidic devices and methods of using the microfluidic devices. The microfluidic devices comprise a fluid streambed with at least one stream, usually at least two streams. The individual streams may be divided by at least substantially 90° walls parallel to each other and desirably perpendicular to the base or floor of the microchannel, or individual streams separated by liquid separators, creating a plurality of microchannels having parallel regions. Disposed on each side of the fluid stream bed are optical elements comprising a first reflective wall for receiving a light beam and directing the light beam through the fluid stream bed and a second reflective wall for receiving the light beam from the fluid stream bed and directing the light beam to a light waste dump.

To produce the microfluidic devices, a positive form (same structure as the final product) is fabricated, which form is used to make a mold for molding microfluidic devices from plastics. The positive form is fabricated by initially providing differential protective coatings over sites of different microstructures using appropriate masking and protective coatings, followed by deep etching the different microstructures independently after differential removal of the protective coatings. The resulting devices may be used in microfluidic operations, where the fluid streambed of parallel streams is used to detect fluorescence from a fluorophore present in the streambed region. A light source directs light through the fluid streambed by means of the optical elements and the fluorescent light is detected normal to the direction of the light beam. In this way, the signal-to-noise ratio is greatly enhanced, interference from fluorescence of the substrate used to produce the device is minimized and simple optical excitation and emission detection systems may be employed.

In producing the microfluidic devices, a form is fabricated from which a mold can be produced. The form is conveniently made from a silicon wafer using microfabrication techniques. The subject method for preparing the form employs a planar masking process for etching deep silicon structures with different cross-sectional profiles that allows patterning of multiple structures before etching while the wafer surface is still planar. The process also provides protection for the previously etched structures during the later etching steps using selective thin-film deposition/growth and, therefore eliminates photoresist spin coating on deep etched structures. In carrying out the process, the channels are produced at one stage and the optical elements at another stage, by employing appropriate masking, protective coatings and etching.

The methodology uses semiconductor lithographic technology. The process involves forming and partially removing layers of silicon dioxide and silicon nitride, enlisting the use of photoresist layers as masks and etching portions of the underlying substrate and/or protective silicon oxide/nitride coatings unprotected by the photoresist. Chemical vapor deposition is employed for providing protective layers of silicon nitride, where layers of silicon oxide and silicon nitride may be differentially removed. The method is described in greater detail in reference to FIG. 2, where the device has walls for separating the different streams in the fluid streambed.

The process is used to produce silicon chips having microstructures in said silicon chip of different cross-sections and depths of greater than about 5 $\mu$m, usually greater than about 10 $\mu$m and may be 100 $\mu$m or more, where depths of 5 $\mu$m create problems of having a uniform photoresist coated using spin coating. The method comprises the steps of: growing silicon dioxide on both sides of a silicon wafer; spin-coating both sides of said wafer with photoresist; photolithographically patterning a first side of said wafer to define sites for at least one of a first set of microstructures;

etching said silicon dioxide layer at sites above areas to be etched to form at least one of a first set of microstructures; stripping said photoresist from said wafer; depositing a silicon nitride layer on both sides of said silicon wafer; spin-coating on both sides of said wafer with photoresist; photolithographically patterning said first side of said wafer to define sites for at least one of a second set of microstructures having a different cross-section from said first set of microstructures; etching said silicon nitride layer at sites above areas to be etched to form said second set of microstructures and silicon dioxide underneath said silicon nitride layer to expose said silicon wafer;

etching said silicon wafer to form at least one of said second microstructures; coating exposed portions of said wafer with silicon dioxide; removing remaining portions of said silicon nitride layer and exposing said wafer at said sites of said at least one of a first set of microstructures; and etching said silicon wafer to form said first microstructures.

By using the process described above, one may prepare devices, where a plurality of liquid streams are irradiated orthogonally to their direction of flow. The device substrate will usually be of a thickness in the range of about 0.2 mm to 1 cm, more usually 1 mm to 5 mm. The substrate will usually be enclosed with a transparent plastic film of from about 5 to 100 $\mu$m thickness. The plurality of liquid streams may be separated by walls constructed in the device or by sheath flow, where the device provides a liquid stream to separate the liquid streams comprising the fluorophore to be measured. Each of the devices will have two optical elements on opposite sides of the liquid streams to be irradiated. Generally, the optical elements will be separated by at least about 0.1 mm, more usually at least about 1 mm, and not more than about 25 mm, usually not more than about 10 mm. The spacing between the optical elements will depend upon the number of liquid streams to be irradiated, whether the streams are separated by liquid or solid spacers, the width of the streams, the nature of the light source, the diffusion of the light beam, and the like. There will generally be at least 2 streams between optical elements, more usually at least about 3 streams, and not more than about 12 streams, usually not more than about 10 streams. By using a multiplicity of optical elements on each side of a group of streams, one can provide for as many streams as one wishes to have irradiated. Since each optical element may have two reflective sides, one side may be used for irradiation of the streams and the other side may be used to direct the light from a different optical element, which light has passed through the streams, to a waste light dump. In an alternative embodiment, the optical element for directing light to a waste light dump is not required where the light will be dispersed within the substrate of the device.

The optical element is a channel, which may or may not be the length of the liquid stream. The optical element will have a wall, which reflects the light beam. The depth and length of the optical element need only be sufficient to fulfill its function of directing a light beam. The length of the optical element will usually be at least about 1 mm and not more than the length of the stream. The depth will usually be at least about 10% of the depth of the streambed and up to and including the depth of the streambed, although it may be extended further, if desired. Reflection may be as a result of a difference in refractive index between the substrate and the contents of the optical element channel, a reflecting surface inside the channel, e.g. aluminum, silver, etc., or other means for light transfer. Where the optical element channel is between two groups of streams, it will have two reflecting walls, one normally for directing the light beam into the streams and the other for reflecting the light received from the streams into a light dump. While it is not necessary to have the walls at a 45° angle to the planar surface of the device, this angle is the most convenient, since the light source can be directed normal to the surface of the device and will be reflected at a 90° angle to the light beam from the light source. Otherwise, the light source will be placed at an angle to the optical element channel wall, which provides that the light be reflected in a line or plane parallel to the surface of the device. The angle of the wall will usually be in the range of about 45±15°.

When solid walls are present in the streambed, they will have a width of about 0.1 to 100 $\mu$m, more usually about 1 to 50 $\mu$m. The height of the wall will generally be about 2 to 500 $\mu$m, more usually about 5 to 100 $\mu$m, while the spacing between the walls forming the channels will usually be in the range of about 5 to 500 µm, more usually about 10 to 200 µm. When solid walls are not present in the streambed, namely the streams are separated by liquid walls or streams using sheath flow, separation between streams will be at least about 10 µm, more usually at least about 20 µm, and not more than about 100 µm, usually not more than about 50 µm.

The subject devices find particular use with multiplexed devices, which produce a plurality of streams having a fluorescent entity for detection. These devices are exemplified by electrokinetic devices, where the electrokinetic devices have a plurality of units, each unit producing an independent stream for analysis. The subject device may be part of an electrokinetic device, so as to be integrated with the substrate used for forming the electrokinetic units. The electrokinetic devices are characterized by having a channel, which will feed the stream into the detection device of the subject invention. In this instance, the walls of the electrokinetic device may have the same orientation as the walls of the electrokinetic device or the electrokinetic wall channels be tapered to join with the detection device walls.

In the situation with the liquid walls or streams, the streams from the electrokinetic units will generally be tapered down to reduce the length of the irradiation beam through the streams. The electrokinetic device capillary channels will generally have a width in the range of about 10 to 500 µm, where the walls or spacing between the channels will usually be in the range of about 10 to 1000µ, more usually in the range of about 100 to 500 µm. The tapering area will generally reduce the cross-section of the capillary channels and walls by at least about 30%, preferably at least about 50% and may result in a reduction of 75% or more. The tapering area will have angled sides, where the angle may vary in the range of about 5 to 65°, usually about 45°±15°. The distance between the outlets from the capillary channels and the detection region in the streambed will generally be at least about 0.1 mm, more usually at least about 1 mm and not more than about 10 mm, generally being from about 1 to 5 mm, being controlled by the angle of narrowing, the width of the detection region, the width of the channel area feeding the detection region, the depth of the stream bed and the volume of liquid exiting from the capillary channels into the streambed. The width of the detection region will be in the range of about 0.2 to 50 mm, more usually about 0.5 to 20 mm.

The irradiation region will normally be only a small portion of the stream bed channel, which stream bed channel may be straight or tortuous and of the same or different dimensions from the region of the channels in the irradiation region. Where the stream bed does not have dividing walls, the streams emanating from the capillary channels will generally have a stream width in the range of about 0.1 to 50µ, more usually about 1 to 20µ. There will be at least one stream between optical elements and not more than about 100, usually not more than about 50, generally in the range of about 5 to 50. As discussed previously, the number of streams will be controlled by the effectiveness of the radiation beam and its ability to remain sharp while passing through the streams to ensure a predetermined area of exposure of a desired level of intensity.

There may be one or a plurality of groups of streams bordered by optical elements. For a device, there will be at least one group and there may be two or more, where the groups may be in a single line or be distributed throughout a wafer having a plurality of capillary electrokinetic units. Each of the capillary electrokinetic units will usually have at least three reservoirs and two intersecting channels, where the intersections may be a cross-intersection or a T-intersection. Of course, the units may be much more sophisticated, where a greater number of chambers and channels may be involved, including mixing chambers, additional reservoirs, separation channels, injection channels, etc. Also, there will usually be at least three, usually at least four electrodes, where the electrodes are used to create electrical fields in the channels to move particles by electrokinesis, which includes electrophoresis and electroosmotic force or flow ("EOF").

The subject devices may be prepared as follows. A silicon wafer cut about 9.74° off the <100> orientation is employed to form the (opposite configuration from the final product), which may then be used to produce a negative mold for forming the devices in plastic. The first step is growing a silicon dioxide layer on at least one surface of said silicon wafer. This is followed by photolithographically etching one side of said wafer to remove said silicon dioxide at predetermined sites for channel formation. The silicon wafer is then coated on at least the side in which the channels are to be formed with silicon nitride. To form an optical channel, the channel side is photolithographically etched to expose the silicon at an optical channel site, followed by etching the optical channel site with anisotropic silicon etchant, e.g. hydroxide (5 to 40%) at an elevated temperature (40 to 100° C.) to produce a V-shaped groove at a 45° angle. The exposed silicon in the optical channel is oxidized to silicon oxide, followed by removing remaining silicon nitride and etching the silicon wafer through said silicon dioxide layer to form channels with 90° separating walls. The resulting positive mold may then be used to produce a negative mold to be used for fabricating the subject devices. In an alternative approach, the wafer substrate may be aluminum or some other appropriate composition where microfeatures are cut into the substrate through diamond ruling or turning.

Figure 1B:
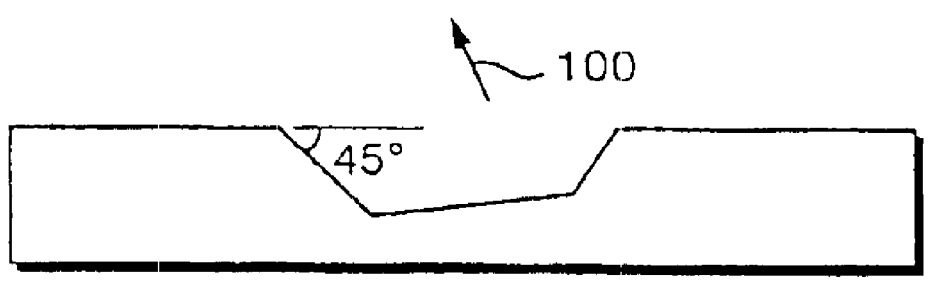
Figure 2A:
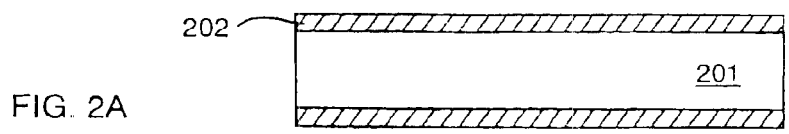
FIGS. 2a–p are diagrammatic views of a silicon wafer during the stages of the processing of the wafer.
Figure 2B:
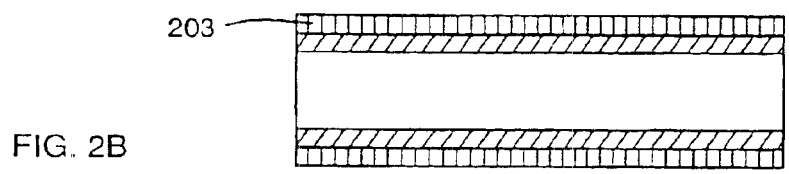
Figure 2C:
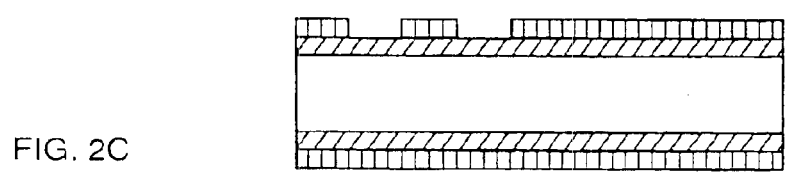
Figure 2D:
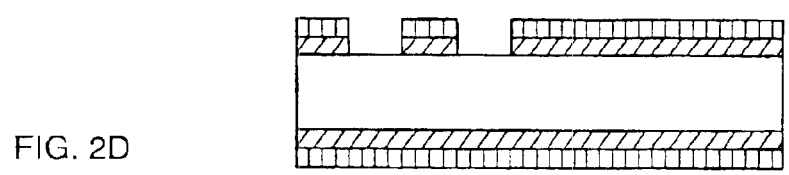
Figure 2E:
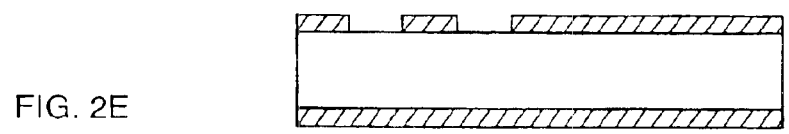
Figure 2F:
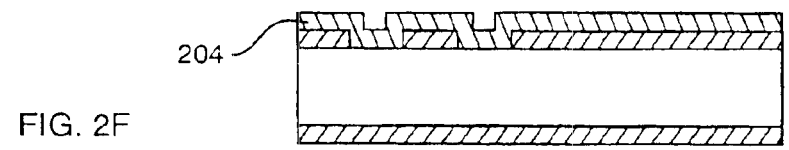
Figure 2G:
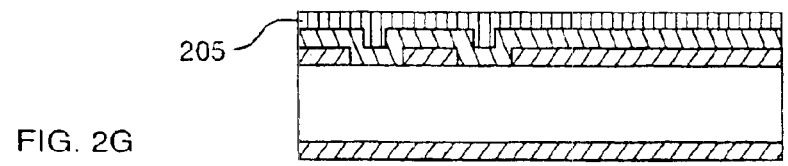
Figure 2H:
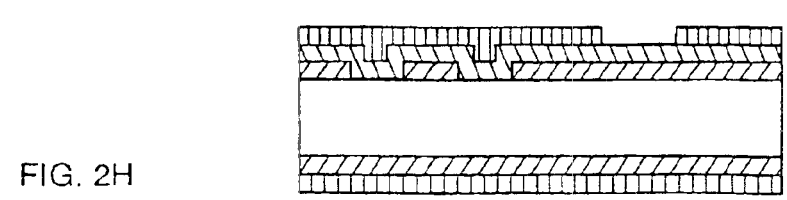
Figure 2I:
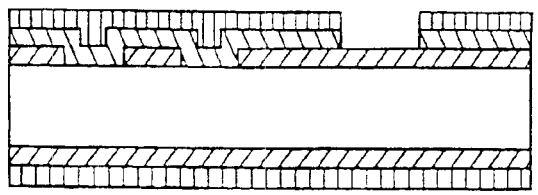
Figure 2J:
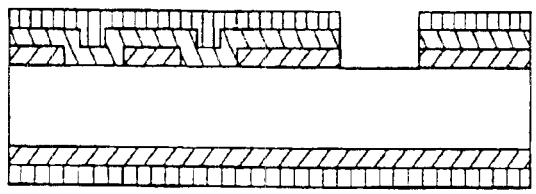
Figure 2K:
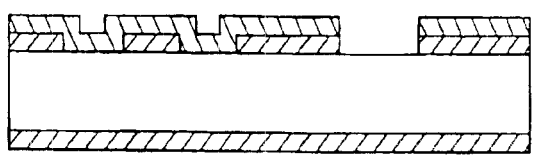
Figure 2L:
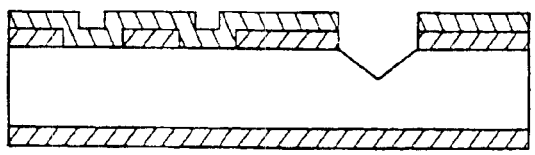
Figure 2M:
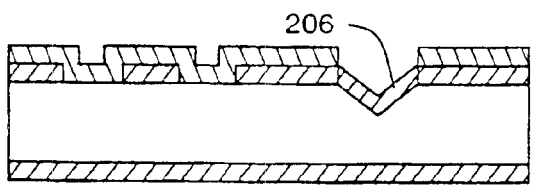
Figure 2N:
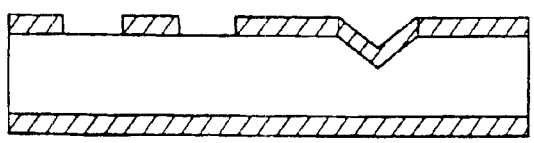
Figure 2O:
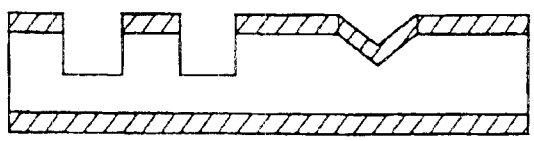
Figure 2P:

To demonstrate the subject invention a chip was prepared as follows:

In FIGS. 1a and 1b are side diagrammatic views of a wafer indicating the angles resulting from etching, where the wall angle varies with the manner in which the wafer is etched. In the common wet etching of <100> silicon wafers, the angle formed between <100> and <111> is 54.74° as shown in FIG. 1(a). To make a 45° angle, the approach of using wafers that were cut 9.74° off the <100> orientation was used. Such wafers were purchased from Virginia Semiconductors.

FIG. 2 shows the fabrication process. First, a 0.2–3 µm (2 µm; the actual exemplification will be indicated in parentheses) thick silicon dioxide layer 202 (FIG. 2(a)) is thermally grown on both sides of a silicon wafer 201. Then, 0.1–4 µm (2 µm) thick Shipley S1818 photoresist 203 is spin-coated on both sides of the wafer, as shown in FIG. 2(b). The photoresist layer 203 on the wafer front side is photolithographically patterned (FIG. 2(c)). The silicon dioxide layer 202 then is etched (FIG. 2(d)) in a hydrofluoric acid solution buffered with ammonium fluoride, using photoresist layer 203 as the mask. The photoresist layer 203 at the back side of the wafer protects the silicon dioxide layer 202 from being etched. After the photoresist layer 203 is stripped, the wafer 201 is left with the silicon dioxide layer 202 shown in FIG. 2(e). In FIG. 2(f), 0.2–2 µm (0.5 µm) thick silicon nitride layer 204 is deposited on both sides of the silicon wafer 201 using low pressure chemical vapor deposition (LPCVD). Another layer of photoresist 205 is spun on both sides of the wafer (FIG. 2(g)) and photolithographically patterned (FIG. 2(h)). The silicon nitride layer 204 is etched using $SF_6/O_2$ plasma etching process with photoresist layer 205 as the mask shown in FIG. 2(i). In FIG. 2(j), the underlying silicon dioxide layer 202 is etched in hydrofluoric acid solution buffered with ammonium fluoride. The photoresist layer 205 is stripped (FIG. 2(k)). The wafer 201 is then etched in 5–40% (20%) potassium hydroxide solution at 40–100° C. (60° C.) (FIG. 2(l)) with both silicon dioxide 202 and silicon nitride 204 as the mask layer. A 50 μm deep V-shape groove with one angle of 45° is formed. In FIG. 2(m), another 2 μm thick silicon dioxide layer 206 is grown on the wafer. Because most of the wafer surface is covered with silicon nitride layer 204, only the exposed V groove silicon surface will be oxidized due to the extremely low oxidization rate of silicon nitride surface. This layer of silicon dioxide layer 206 protects the structures etched in the previous steps from being etched in the later etching steps. In FIG. 2(n), the silicon nitride layer 204 is etched using $SF_6/O_2$ plasma etching without using a mask layer. The $SF_6/O_2$ plasma etching process has relatively high etching selectivity of silicon nitride 204 over silicon dioxide 202 and 206. Because of this, the silicon nitride layer 204 is completely removed while the silicon dioxide layer 202 and 206 is not etched significantly. The silicon wafer 201 is then etched (FIG. 2(o)) using a deep reactive ion etching (DRIE) process to form 50 μm deep channels with vertical sidewalls. Finally, the silicon dioxide layer 202 and 206 is stripped (FIG. 2(p)).

Figure 3:
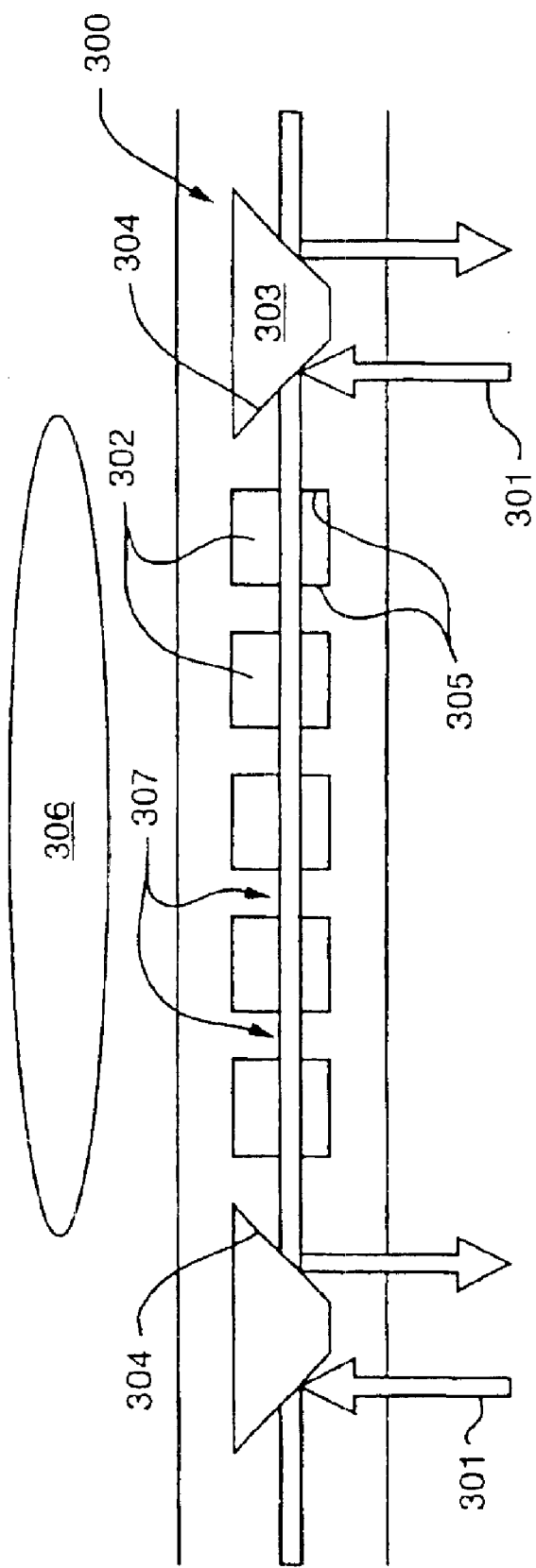
FIG. 3 is a diagrammatic view of a group of electrokinetic capillary channels with two optical elements.

In FIG. 3 is a diagrammatic view of a group of channels with two optical elements. The device 300 has several light beams 301 from light sources (not shown). The light beams 301 are conveniently a laser beam. The device 300 has microfabricated capillary channels 302 and microfabricated optical channels 303, having walls 304, which are shown at a 45° angle. The microfabricated optic 303 is a microfluidic channel, where reflection may be accomplished by coating the surface of the channel with a reflective layer, e.g. aluminum, or the channeled may be filled with air or other material of a different refractive index from the wall material, such that total internal reflection occurs when the laser beam strikes the wall 304 surface. The wall 304 should be optically flat. The channel surfaces or walls 305 should also be substantially optically flat and at a 90° angle to the planar surface of device 300 and, therefore, normal to the laser beam propagation 301. With fluorophores in the channels 302, fluorescence emission is detected perpendicular to the device 300 by an optical system 306. Any convenient optical detection system may be employed, e.g. a CCD, photocells, photodiode, photomultiplier tubes etc. The autofluorescence from the walls 307 separating the channels 302 will provide a very small contribution to the fluorescence emitted from the channel 302.

Figure 4:
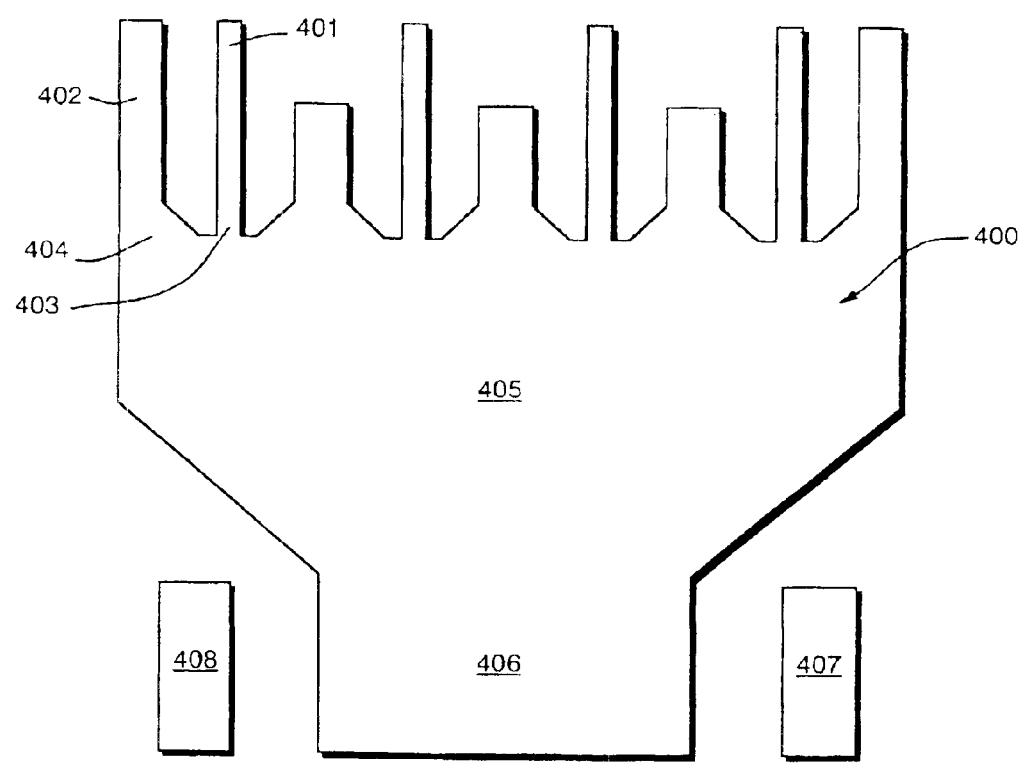
FIG. 4 is a diagrammatic view of a device with a plurality of sample channels interspersed with sheath flow channels.

In FIG. 4, the device 400 comprises a plurality of sample channels 401 interspersed with sheath flow channels 402. The sample channels 401 have outlets 403 and the sheath flow channels 402 have outlets 404 for directing the flow of liquid into streambed 405. For the most part, the liquid in sample channels 401 will be an aqueous electrically conductive liquid, having a component to be measured. Frequently, the liquid carrier will be an aqueous buffer. The sheath flow liquid may be the same liquid as the carrier or a different liquid, having the same or different composition and viscosity. The rate of flow of the streams of sample liquid and sheath flow liquid will be adjusted to provide the desired width of the sample liquid in the detection region 406 and the desired spacing between sample streams. Optical elements 407 and 408 are positioned on opposite sides of the detection region 406, whereby light reflected from optical element 407 is propagated through the detection region 406 and the sample streams and reflected into a light dump by optical element 408. Fluorescence emitted from detection region 406 is detected by an appropriate fluorimetric detection system, not shown.

Figure 6:
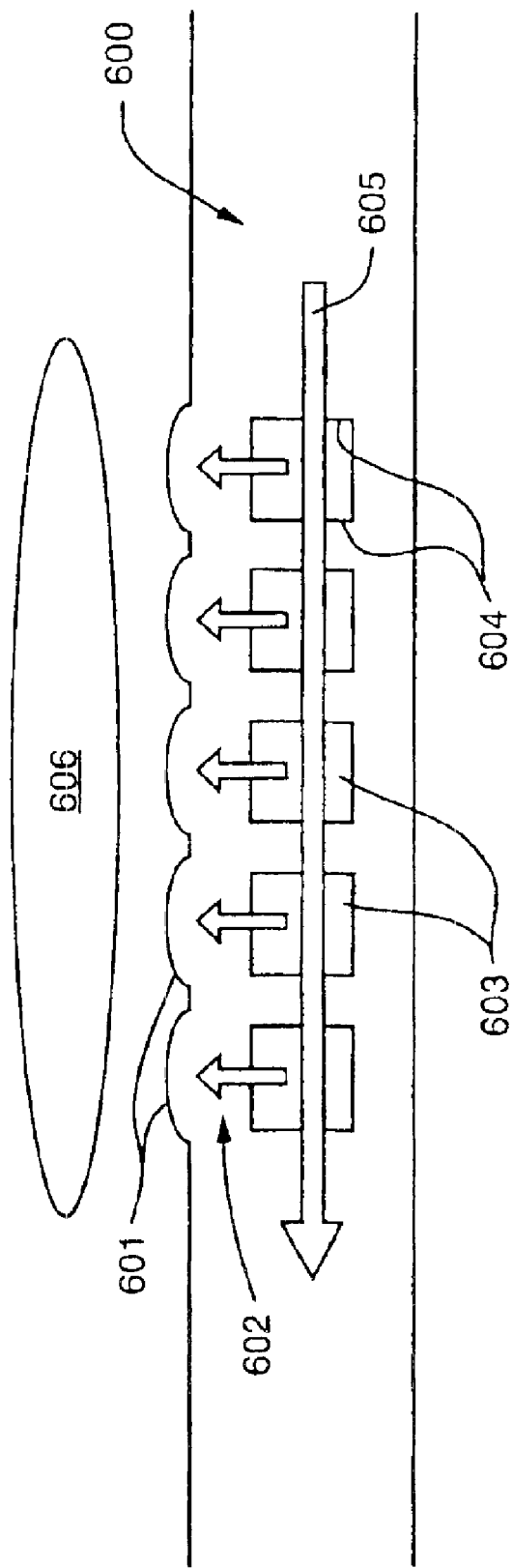
FIG. 6 shows diagrammatically a microfluidic device having several intergrated microlenses.

The device may be modified by having microlenses integrated into the top plate. As seen in FIG. 6, the microfabricated device may have several inegrated microlenses 601 incorporated into the top plate to substantially capture more fluorescence 602 excited within the microfluidic channels 603. The walls 604 of channels 602 may or may not be substantially optically flat and may or may not be precisely at a 90° angle, usually deviating at most by about 10° from the planar surface of the device 600. The light beam 605 used to excite the fluorescence within the microfluidic channels may propagated through the channels at an angle substantially parallel to the planar surface of the device or deviate from such angle, usually by not more than about 10°. In addition to the microlenses 601, further focussing of the light from the individual channels onto a detector array or fiber optic array leading to a detector array may be implemented by a focussing lens system 606.

Figure 5:
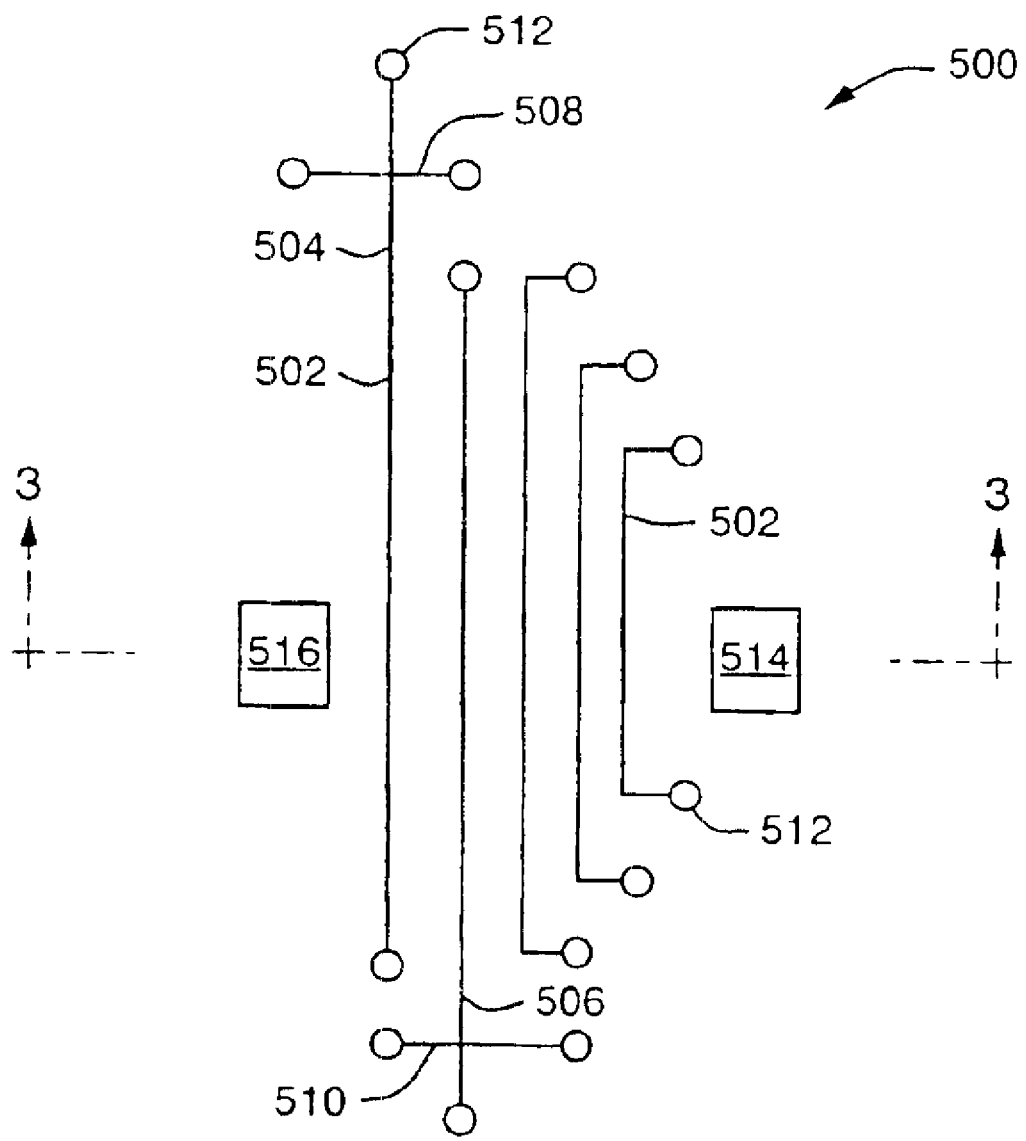
FIG. 5 is a diagrammatic plan view of an exemplary capillary channel and optical channel layout.

In FIG. 5 is a diagrammatic plan view of the layout of the chip as employed in the subject invention and as depicted in cross-section in FIG. 3. The microfluidic device 500 has a plurality of capillary channels with differing lengths. Two of the microfluidic channels 504 and 506 have injection cross-channels 508 and 510, respectively. Each of the channels has reservoirs 512 at opposite ends of the channel, in which electrodes, not shown, are placed. By appropriate activation of the electrodes, either electroosmotic flow or electrophoretic flow occurs in the channels 502. Optical channels 514 and 516 are placed on opposite sides of channels 502, where laser light from a laser source, not shown, may be directed from the wall of optical channel 514 through the channels 512 and reflected to a waste dump by optical channel 516. A fluorescent detector, not shown, detects fluorescence in the region of the light path between optical channels 514 and 516.

In the above process, the two etching steps to create the V grooves and the vertical sidewall channels can be swapped without changing any other processing steps. Also, other techniques such as aligning wafers to different orientations can be used to create the 45° angle channels. The chip design is as depicted in FIG. 5, where the chip dimensions are 4 in square; the cast chips were enclosed with Mitsubishi films UN6.53.91 and UN6.53.92.

To test the effectiveness of the devices for irradiation of fluorophores and reduction of autofluorescence of the chips, a video was taken of the events using a camera attached to an inverted epifluorescence microscope with 488 nm laser at 6 mW and viewing through an OG bandpass filter. A 100 μM TAMRA solution in TBE was employed and diluted in TBE to the final concentration. All images were viewed through a 10×10.45 objective, except the phase contrast image, which used a 20×10.45/Ph 1 objective.

Clear bands were observed with both 1 μM and 10 nM TAMRA. Little, if any, autofluorescence was observed. With dye in the channels, a sharp band of fluorescence is observed at the sight where the light beam passes through the TAMRA containing solution, with the fluorescence intensity related to the concentration of the fluorophore. Above the chip, a scatter pattern is observed, probably resulting from multiple reflections in the chip.

It is evident from the above results that the subject invention provides for an efficient method for irradiating fluorophores in microchannels or capillary channels, or it parallel streams lacking physical dividers. The irradiation light can be efficiently directed across a number of streams without causing significant autofluorescence and provides for sharp bands in the detection region. The devices can be readily manufactured to provide the desired channels and then be used for performing a variety of operations in a channel where the outcome is a fluorescent signal.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An irradiation device for irradiating a plurality of streams of capillary dimensions, said device comprising:
   a substrate comprising a streambed for receiving a plurality of liquid streams of capillary dimensions;
   capillaries in liquid transferring relationship with said streambed for forming said streams;
   optical channels on opposite sides of said stream bed having reflecting walls confronting said streambed and parallel to the direction of said streams, one of said reflecting walls positioned for receiving light from light source and directing said light orthogonally through said streambed, and the other of said optical channels for reflecting said light to a light dump.

2. An irradiation device according to claim 1, further comprising a laser light source positioned at an angle to said reflecting wall to direct light orthogonally from said reflecting wall.

3. An irradiation device according to claim 2, wherein said reflecting walls are at 45° to the base of said device.

4. An irradiation device according to claim 1, wherein said reflecting walls are at 45° to the base of said device.

5. An irradiation device according to claim 1, wherein said streambed further comprises separating walls for physically separating said streams in said streambed, said separating walls at a 90° to said streambed.

6. An irradiation device according to claim 1, further comprising sheath flow capillaries interspersed between said stream capillaries to provide liquid separation between said streams.

7. An irradiation device for irradiating a plurality of streams of capillary dimensions, said device comprising:
   a substrate comprising a streambed for receiving a plurality of liquid streams of capillary dimensions, said streambed divided into a plurality of capillary-sized zones by perpendicular walls;
   capillaries in liquid transferring relationship with said streambed for forming and directing individual streams into said zones;
   electrokinetic means for moving said streams from said capillaries into said streambed; and
   optical channels on opposite sides of said stream bed having reflecting walls confronting said streambed and parallel to the direction of said streams, one of said reflecting walls positioned for receiving light from light source and directing said light orthogonally through said streambed, and the other of said optical channels for reflecting said light to a light dump.

8. An irradiation device according to claim 7, wherein said reflecting walls are coated with a reflecting coating.

9. An irradiation device according to claim 7, wherein said optical channels are filled with air.

10. An irradiation device according to claim 7, wherein said substrate is plastic and said stream bed is enclosed.

11. An irradiation device for irradiating a plurality of streams of capillary dimensions, said device comprising:
    a substrate comprising a streambed for receiving a plurality of liquid streams of capillary dimensions;
    a cover enclosing said streambed;
    capillaries in liquid transferring relationship with said streambed for forming said streams;
    electrokinetic means for moving said streams from said capillaries into said streambed;
    sheath flow capillaries interspersed between said capillaries;
    a reservoir in fluid transfer relationship with said sheath flow capillaries; and
    optical channels on opposite sides of said stream bed having reflecting walls confronting said streambed and parallel to the direction of said streams, one of said reflecting walls positioned for receiving light from light source and directing said light orthogonally through said streambed, and the other of said optical charnels for reflecting said light to a light dump.

12. An irradiation device according to claim 11, wherein said reflecting walls are have a reflecting coating.

13. An irradiation device according to claim 11, wherein said optical channels are filled with air.

14. An irradiation device for irradiating a stream of capillary dimensions, said device comprising:
    a substrate comprising a streambed for receiving a liquid stream of capillary dimensions;
    one or more capillaries in liquid transferring relationship with said streambed for forming said stream;
    an optical channel on one side of said stream bed having reflecting walls confronting said streambed and parallel to the direction of said stream, one of said reflecting walls positioned for receiving light from light source and directing said light orthogonally through said streambed.

15. An irradiation device according to claim 14 further comprising an optical channel on the other side of said stream bed having reflecting walls confronting said streambed and parallel to the direction of said stream, one of said reflecting walls positioned for reflecting light from said streambed to a light dump.

16. An irradiation device according to claim 14 wherein said substrate comprises a streambed for receiving a plurality of liquid streams of capillary dimensions for irradiation.

17. An irradiation device according to claim 15 wherein said substrate comprises a streambed for receiving a plurality of liquid streams of capillary dimensions for irradiation.

* * * * *